United States Patent
Knoell (10) Patent No.: US 9,277,917 B2
(45) Date of Patent: Mar. 8, 2016

(54) LATTICE STITCH SURGICAL TENSIONING DEVICE WITH HORIZONTAL PATENCY

(71) Applicant: Keith Knoell, Crozet, VA (US)

(72) Inventor: Keith Knoell, Crozet, VA (US)

(*) Notice: Subject to any disclaimer, the term of this patent is extended or adjusted under 35 U.S.C. 154(b) by 236 days.

(21) Appl. No.: 13/793,821

(22) Filed: Mar. 11, 2013

(65) Prior Publication Data
US 2013/0261646 A1    Oct. 3, 2013

Related U.S. Application Data

(60) Provisional application No. 61/609,107, filed on Mar. 9, 2012.

(51) Int. Cl.
*A61B 17/04* (2006.01)

(52) U.S. Cl.
CPC ............ *A61B 17/0482* (2013.01); *A61B 17/04* (2013.01); *A61B 17/0466* (2013.01); *A61B 2017/0406* (2013.01)

(58) Field of Classification Search
CPC .......... A61B 17/0482; A61B 17/0401; A61B 2017/00663; A61B 17/04; A61B 17/0466
USPC ................................. 606/139, 232
See application file for complete search history.

(56) References Cited

U.S. PATENT DOCUMENTS

| | | |
|---|---|---|
| 2005/0283192 A1 | 12/2005 | Torrie et al. |
| 2007/0225710 A1* | 9/2007 | Jahng et al. ............ 606/61 |
| 2010/0121348 A1* | 5/2010 | van der Burg et al. ...... 606/139 |

OTHER PUBLICATIONS

Internal Search Report issued May 21, 2013 in corresponding PCT Application No. PCT/US2013/030205.

* cited by examiner

*Primary Examiner* — Victor Nguyen
(74) *Attorney, Agent, or Firm* — Sughrue Mion, PLLC (57) ABSTRACT

A lattice stitch surgical tension-limiting device, designed to be used in lattice stitch repair of wounds in biologic tissue. The device is tied to the surface of biologic tissue to be repaired by a lattice stitch. The device is designed to limit the tension in the lattice stitch, to allow placement of the lattice stitch without the need of an assistant and "instrument tie", to help displace tension away from the surface of the body tissues, to enhance the properties of the lattice stitch in tissue shear reduction, and manage rotational forces affecting the repair as the lattice stitch draws the wound together to a closed condition. The device remains on the tissue surface during the wound healing period and is removed with the lattice stitch when wound healing is complete.

5 Claims, 4 Drawing Sheets

LATTICE STITCH SURGICAL TENSIONING DEVICE WITH HORIZONTAL PATENCY

This application claims the benefit of U.S. provisional patent application U.S. Application No. 61/609,107, filed Mar. 9, 2012.

FIELD OF THE INVENTION

This invention relates generally to devices that can be used to facilitate placement and proper tensioning of sutures used to form a lattice stitch. The devices also function to separate suture material from the surface of body tissues to help reduce the potential of scarring from suture pressure.

BACKGROUND OF THE INVENTION

The lattice stitch is a suture-based method of surgical repair that distributes biologic tissue tension throughout the full thickness of the wound in both parallel and perpendicular directions from the wound edge. It is ideally, but not exclusively, suited for closure of atrophic skin and wounds under high tension and can be effectively used as a salvage stitch to repair wounds with secondary tissue tears (tears in wounds that have occurred as a result of failure of a wound repair using a closure other than the lattice stitch).

The lattice stitch is formed by first placing a pair of "anchor" stitches in opposed positions parallel to the wound edge, one on each side of the wound. The anchor stitches are placed with sufficient tension to minimize slack, while avoiding excessive tightening/strangulation of the skin. Next, a "closing" stitch is passed through the skin and is looped around the anchor stitches. The closing stitch is then drawn together at the surface of the tissue and is tied at the center of the wound. It is possible to place multiple closing stitches around a single pair of anchor stitches for additional support of the repair, at the surgeon's discretion.

In a lattice stitch repair, the closing stitch is preferably looped completely around each anchor stitch within the tissues, before the stitch is tied at the surface of the wound, thus, drawing the wound together to a closed condition. This arrangement optimizes stitch function and efficacy. Alternate arrangements of the closing stitch and anchor stitches in a lattice stitch repair include those where the closing stitch is passed through the loop of one or both anchor stitches, in the tissues, before the closing stitch is tied at the surface of the wound. Said alternate lattice stitch arrangements are not as effective at displacing wound tension or shear, in comparison to the preferred embodiment of the lattice stitch repair.

In the preferred embodiment of the lattice stitch, closing tension across the wound borne by the closing stitch is distributed away from the plane of closure in a direction parallel to the wound edge throughout the full thickness of the repair by the anchor stitches through a process called "dynamic vectoring." In this process, the lattice stitch adjusts its three dimensional structural configuration to accommodate forces acting on the repair during wound closure and throughout the healing period. Tissue shear forces during closure of a lattice stitch are largely avoided since the closing stitch is drawn primarily over anchor stitches during closure. Leverage for the closure is provided for the closing stitch by the anchor stitches which act as fulcrums, allowing a great degree of force to be exerted on the closure with little effort. Unlike staples, the lattice stitch can be placed at significantly variable distances from the wound edge and can use substantial subcutaneous tissue support, depending on the needs of the closure. Suture removal is easy because the stitch does not "sink" into the skin; a common problem with the vertical mattress type closures typically used in high tension wound repairs. The lattice stitch is versatile and can be used singly as a support element in repairs where other stitching methods are used, or in plurality as part of a complex lattice closure in cases where a greater distribution of tension is desired.

Despite the stated advantages of the lattice stitch, there are some limitations of this repair technique. The anchor stitches of a lattice stitch must be properly tensioned for optimal function, and this can be difficult to achieve under certain conditions. Use of an "instrument tie" with the help of an assistant, can facilitate proper tensioning of the anchor stitches, but can be a challenge to arrange in a busy office or emergency room setting. Excessive tension in the anchor stitches inhibits optimal functioning of the lattice stitch and may contribute to wound ischemia. Slack anchor stitches, on the other hand, can lead to unnecessary stretching of the tissue behind the anchors when the closing stitch draws the wound together and can lead to small tissue tears behind the anchors by the closing stitch, especially in repairs of extremely delicate tissue. Pressure from the lattice stitch on the surface of the skin, especially in high-tension closures, might lead to the formation of scar tissue under the sutures ("suture tracks"). Although this problem is not unique to the lattice stitch, it could be seen more commonly with this method of repair since the lattice stitch is well suited for high-tension closures.

A need exists, therefore, for a device that can facilitate proper tensioning of the (lattice) anchor stitches without the need for an assistant/instrument tie whilst preserving the dynamic vectoring properties of the lattice stitch; and, to separate the suture material of the lattice stitch from the surface of the tissues to help reduce the likelihood of scarring. The device should also manage any frictional and rotational forces in a lattice stitch repair that can occur as the closing stitch draws the wound to a closed condition.

Various apparatus and suture based methods for biologic tissue repair are known in the patented prior art as evidenced by Bonutti U.S. Pat. No. 5,403,348; Bonutti U.S. Pat. No. 5,549,631; and Gibson U.S. Pat. No. 6,063,106.

Bonutti U.S. Pat. No. 5,403,348 discloses an apparatus that is adapted to be received at least partially in body tissue, for purpose of securing a suture in the body, consisting of a cylindrical tissue anchor with a smooth outer surface, and an attached suture means. Bonutti U.S. Pat. No. 5,549,631 is a continuation of Bonutti U.S. Pat. No. 5,403,348 that teaches a method for closing a discontinuity in biologic tissue by moving the tissue anchor described in Bonutti U.S. Pat. No. 5,403,348 into the body tissue by means of a pusher mechanism and an application of force. The anchor must be suitable for implantation in the biologic tissue and must be sufficiently rigid to permit suture retention function and according to the methods governing use of the anchor. The Bonutti method teaches a technique of skin repair that requires subcutaneous access to the wound and a high tolerance of tissue shear at the tissue insertion point of the apparatus at closure. The Bonutti method would not be suitable for applications where use of an implantable anchor device with an associated suture means was inappropriate or unnecessary; in repairs of delicate tissue; in situations where sufficient subcutaneous access to a cutaneous wound was unavailable, or in situations where a pusher mechanism as taught by Bonutti were unavailable.

The Gibson patent teaches a substantially disk shaped tissue spacer including a plurality of apertures for receiving suture thread and a depression in the bottom surface thereof to space the apertures above the surface of the skin to reduce the formulation of granulation tissue in surgical applications such as removal of varicose veins, treatment of chronic ulcerations and hernias, attachment of deep cutaneous structures and positioning of prosthesis under the skin. A disk shaped structure of a design consistent with the Gibson spacer would be incompatible with lattice stitch repair. Such a design would be significantly inflexible in the trans-axial plane (force applied on plane to the edge of the disk) and force applied perpendicular to the edge of the disk structure would result in a rotational stress on the structure, thus limiting use of such a design in applications such as lattice stitch repairs where such properties would be undesirable.

While the prior apparatus and methods operate satisfactorily as intended, they are not particularly effective in repairs involving lattice stitch closures of atrophic tissues, wide wounds, and/or delicate/high tension wounds with limited subcutaneous access, all of which require a reduction of tissue shear forces, accommodation of dynamic vectoring of tissue tension, and management of rotational and frictional force in the repair, in order to avoid tissue tears, ischemia, wound edge inversion, necrosis and/or dehiscence. The above apparatus and methods do not allow an unassisted surgeon to properly tension lattice anchor stitches whilst preserving the dynamic vectoring properties of the lattice stitch; and, by extension, cannot be used to separate the suture material of the lattice stitch from the surface of the tissues to help reduce the likelihood of scarring. The present invention was developed in order to overcome these and other drawbacks by providing a uniquely configured lattice stitch surgical tension-limiting device to complement lattice stitch repairs.

SUMMARY OF THE INVENTION

Accordingly, it is a primary object of the invention to provide a lattice stitch tension-limiting device that allows placement of the lattice stitch without the need of an assistant and "instrument tie", whilst facilitating proper tensioning of the lattice stitch; preserving the dynamic vectoring properties of the lattice stitch; enhancing the leverage of the lattice stitch; helping to reduce tissue shear forces; helping to displace tension away from the surface of the body tissues; and, managing frictional and rotational stresses that can occur in lattice stitch wound repairs that could lead to wound edge inversion as the wound is drawn together to a closed condition.

The device, preferably, consists of an elongated semi-flexible primary component with a substantially cylindrical shape and at least one patency extending though the body of the primary component in an orientation substantially perpendicular to a plane extending though the rotational axis of said component, said patency of the primary component being capable of receiving and retaining a portion of suture used to make a lattice stitch; and at least one secondary component encircling a portion of the peripheral surface of the primary component said secondary component being placed in contact with the body tissue to be repaired.

In the preferred embodiment of wound repair using the lattice stitch tension-limiting device, at least one device is provided between each anchor stitch and the tissue layer adjacent to the wound, thus comprising an "anchor stitch/ device" arrangement; each anchor stitch/device arrangement located in opposed positions across the wound, opposite and parallel to the wound edge. The device is not inserted into the tissue to be repaired nor does it exert force on the tissues to enable a repair of said tissue. A closing stitch of the lattice stitch repair is then inserted into the tissue, encircling the opposed anchor stitch/device arrangements. The closing stitch in this configuration is used to draw the wound edges together at the surface of the tissues and is then tied to a closed condition. The device flexes with the anchor stitches on the surface of the tissue toward the wound in a plane parallel to the wound edge, under influence of forces applied by the closing stitch on the device, thus facilitating the process of dynamic vectoring during closure and throughout wound healing.

The elongated cylindrical shape of the primary component of the device provides sufficient support to permit an unassisted surgeon to tie suture material at optimal tension when the device is secured to the surface of the tissues; yet, can also accommodate flexion in a plane parallel to the surface of the wound as when tension is applied to the device. The device provides additional leverage for the repair and helps reduce tissue shear forces from the suture material by acting as a fulcrum for the closing stitch. The device also distributes tension widely over the surface of the skin by separating suture material of the lattice stitch from the surface of the tissue to help prevent suture track scarring.

The secondary component of the device helps distribute tension on the surface of the tissues and helps manage conformational forces acting on a lattice stitch closure as the tension is brought to bear on the repair. Conformational forces in a lattice stitch repair have two major sources: rotational force from friction by the closing stitch on the device as the closing stitch is drawn out of the tissue during closure, and frictional/rotational force from the tissue on the surface of the device as the device is displaced during closure; the portion of the each device nearest the closing stitch travels significantly closer to the wound than the portions nearest each tissue insertion site of the anchor stitches and is subject to proportionally more frictional/rotational force as a result. In lattice stitches where no device is used, conformational forces during closure act primarily on the anchor stitches.

In the preferred embodiment of the invention, the secondary component is capable of movement on the surface of the primary component in a manner independent of the movement of the primary component. In this configuration, conformational forces acting on the device during wound closure are optimally managed by the secondary component of the device as the wound is drawn together to a closed condition. In an alternate aspect of the invention, the secondary component is held in a fixed position relative to the primary component, and the choice of material for the secondary component can help manage conformational forces without compromising the properties of the primary component.

Alternate embodiments of the lattice stitch surgical tension-limiting device can feature grooves, ridges, prominences and fenestrations on various components of the device to help manage suture material, facilitate dynamic vectoring properties of the lattice stitch, and/or to help control the interaction of components in the device or on the tissues as described below. The device is designed to hold the closing stitch in position at closure through the presence and function of certain structural features such as prominences or grooves as described below; or can hold the closing stitch in position by virtue of conformational change in the shape of the device under influence of closing force applied by the closing stitch on the device; or a combination thereof. The device can be constructed with a variety of materials of suitable flexibility and friction characteristics. Examples include, but are not limited to, plastic, silicone and biopolymers. A single material or composite of materials can be used in the construction of the device. In general, the edges of the device are, preferably, slightly rounded to reduce the sharpness. Any embodiment of the device may be impregnated with medications.

DETAILED DESCRIPTION OF THE INVENTION

The lattice stitch surgical tension-limiting device will be described with reference to FIGS. 1-13.

Figure 1:
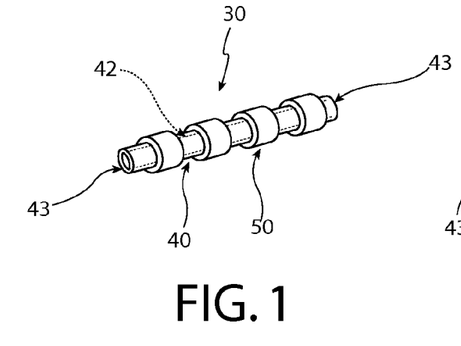
FIG. 1 is a top perspective view of a lattice stitch surgical tension-limiting device according to the invention.

FIG. 1 is a top perspective view of a lattice stitch tension-limiting device 30. More particularly, the device 30 is composed of a primary component 40 and at least one secondary component 50. The primary component has an elongated, semi-flexible and substantially cylindrical configuration and contains at least one patency 42 extending through the body of the component in an orientation substantially perpendicular to a plane extending through the rotational axis of the component. The patency 42 can be used to receive and retain a portion of suture. The primary component 40 contains an interior surface consisting of the surface of the walls of the patency 42 extending to each mouth 43 of the patency 42. The primary component 40 contains an exterior surface that consists of all surfaces except the interior surface. At least one secondary component 50 encircles a portion of the exterior surface of the primary component. The secondary component 50 can be constructed of a material identical to or dissimilar from the material of construction of the primary component 40. In the preferred embodiment of the device, the secondary component 50 is capable of independent movement on the exterior surface of the primary component 40, the secondary component 50 being placed in contact with the surface of the body tissue. In an alternate embodiment, the secondary component 50 can be fixed to the exterior surface of the primary component 40. In this embodiment, the secondary component 50 can be constructed of a different material than the primary component 40. In this configuration, the primary component 40 provides a suitably stable base for tying suture material, whilst the secondary component 50 can be constructed with a softer material for contact with the body tissue surface. If desired, any portion of the device 30 may be impregnated with medications.

Figure 2:
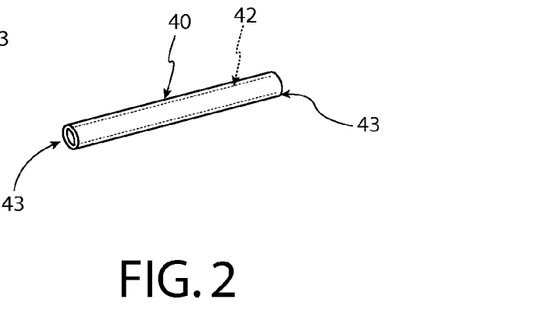
FIG. 2 is a top perspective view of the primary component of FIG. 1.

FIG. 2 is a top perspective view of the primary component 40 of the device of FIG. 1. In this view, the primary component 40 has an elongated, substantially cylindrical configuration that contains a patency 42 extending through the body of the component in an orientation substantially perpendicular to a plane extending through the rotational axis of the component. The primary component 40 contains an interior surface consisting of the surface of the walls of the patency extending to each mouth 43 of the patency. The primary component 40 contains an exterior surface that consists of all surfaces except the interior surface.

Figure 3:
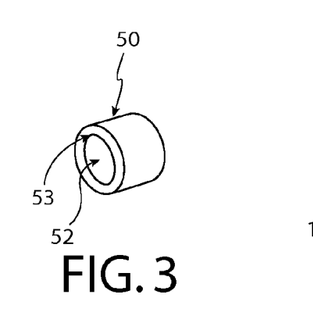
FIG. 3 is a top perspective view of a secondary component of FIG. 1.

FIG. 3 is a top perspective view of the secondary component 50 of the device of FIG. 1. In this view, the secondary component 50, preferably, has a substantially round shape when viewed in cross section with respect to the axis of rotation of the component. The secondary component 50 contains a patency 52 extending through the body of the component. The secondary component 50 contains an interior surface consisting of the surface of the walls of the patency 52, extending to each mouth 53 of the patency 52. The component contains an exterior surface that consists of all surfaces except the interior surface. Alternate aspects of the secondary component shapes can include a cylindrical shape, spherical shape, prolate spheroid shape, dumbbell shape, and cone shape, among others.

Figure 4:
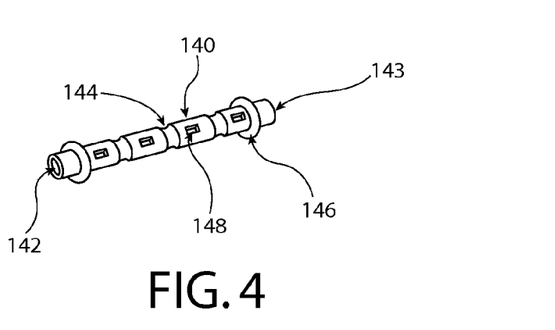
FIG. 4 is top perspective view of an alternate embodiment of a primary component of the lattice stitch surgical tension-limiting device, according to the invention.
Figure 10:
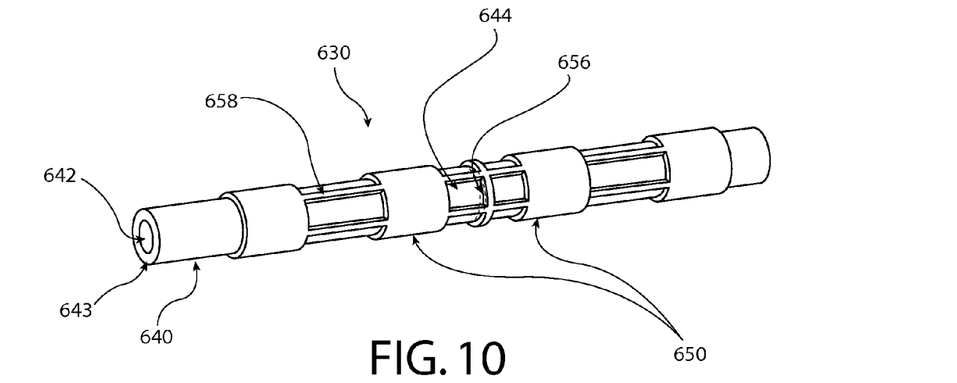
FIG. 10 is another aspect of a lattice stitch surgical tension-limiting device according to the invention.

FIG. 4 is a top perspective view of a further embodiment of the lattice stitch surgical tension-limiting device primary component 40 of FIG. 2 showing a component 140 with a substantially cylindrical configuration that contains a patency 142 extending through the body of the component in an orientation substantially perpendicular to a plane extending through the rotational axis of the component. The primary component 140 contains an interior surface consisting of the surface of the walls of the patency extending to each mouth 143 of the patency. The primary component 140 contains an exterior surface that consists of all surfaces except the interior surface. The component can contain one or more depressions 144 on the exterior surface of the component. Each depression 144 can be formed in the shape of a groove arranged in an orientation substantially along a perimeter arc of the component that can completely encircle the component, as shown, or can be arranged in an orientation substantially parallel to the axis of rotation of the component. The depressions can, alternately, be randomly positioned discrete indentions. Each depression can be used to receive a length of suture or can be used to control the movement of structures along the rotational axis of the component, on the exterior surface of the component as developed below. Each of the depressions 144 may contribute to the overall flexibility of the component to help enable dynamic vectoring to occur in a lattice stitch application. The component can contain one or more prominences 146 on the exterior surface of the component. Each prominence 146 is a convex portion that can be arranged in an orientation substantially along a perimeter arc of the component that can completely encircle the component in a ring-shape, as shown, or can be arranged in an orientation substantially parallel to the axis of rotation of the component. The prominences 146 can be randomly positioned discrete nodules on the exterior surface of the component. Each prominence 146 can be used to receive a length of suture or can be used to control the movement of structures (such as a secondary component) along the rotational axis of the component, on the exterior surface of the component. The component can contain one or more fenestrations 148 located along the body of the component that can create a passage from the exterior surface to the interior surface of the component, perpendicular to the axis of rotation of the component. The fenestrations can be an opening in the body of the component or can be a weakened portion of the component that opens by force, like an old-fashioned rubber change pouch. The fenestrations 148 can be formed of a variety of shapes that can allow the component to change its configuration or overall shape along the axis of rotation as force is applied to the component. A fenestration can be any size and can, thus, can be sufficiently large as to leave only a small tether of material connecting portions of the component bordering the fenestration. In the example shown, the fenestration 148 is a weakened portion that opens by force. In the example of FIG. 10, below, the fenestration is an opening in the body of the component.

Figure 4A:
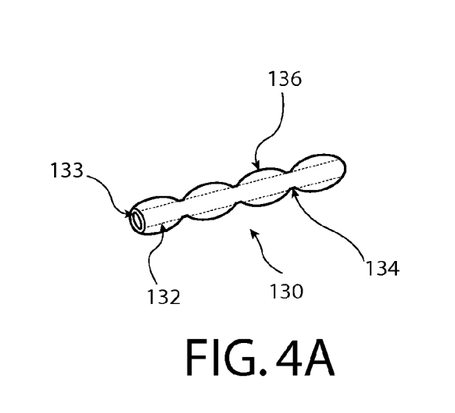
FIG. 4A is a top perspective view of another embodiment of a primary component of the lattice stitch surgical tension-limiting device, according to the invention.

FIG. 4A is another embodiment of the lattice stitch surgical tension-limiting device 40 of FIG. 2 showing a component 130 with a substantially cylindrical configuration that contains a patency 132 extending through the body of the component in an orientation substantially perpendicular to a plane extending through the rotational axis of the component. In this figure, the primary component 130 contains an interior surface consisting of the surface of the walls of the patency extending to each mouth 133 of the patency. The primary component 130 contains an exterior surface that consists of all surfaces except the interior surface. The component contains a plurality of depressions 134 on the exterior surface of the component. Each of the depressions 134 is formed in the shape of a groove. Each depression 134 is arranged in an orientation substantially along a perimeter arc of the component that completely encircles the component. Each depression can be used to receive a length of suture or can be used to control the movement of structures along the rotational axis of the component, on the exterior surface of the component as developed below. The component contains a plurality of prominences 136 on the exterior surface of the component. Each prominence 136 is a convex portion that is arranged in an orientation substantially along a perimeter arc of the component that completely encircles the component. Each prominence 136 can be used to receive a length of suture or can be used to control the movement of structures (such as a secondary component) along the rotational axis of the component, on the exterior surface of the component.

Figure 5:
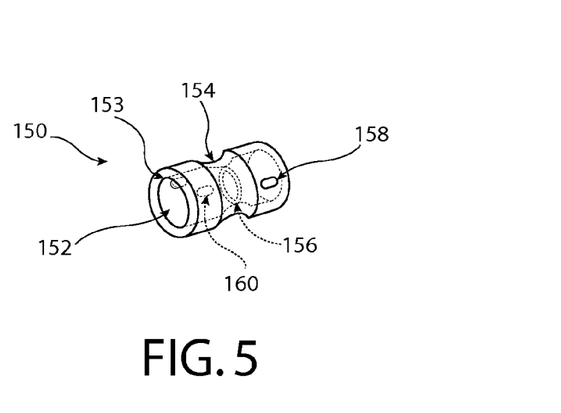
FIG. 5 is top perspective view of an alternate embodiment of a secondary component of the lattice stitch surgical tension-limiting device, according to the invention.

FIG. 5 is a top perspective view of an alternate embodiment of the lattice stitch surgical tension-limiting device secondary component of FIG. 3 showing a secondary component 150, which is similar to secondary component 50, that has a substantially round shape when viewed in cross section with respect to the axis of rotation of the component. The secondary component 150 contains a patency 152 extending through the body of the component. The secondary component 150 contains an interior surface consisting of the surface of the walls of the patency 152, extending to each mouth 153 of the patency 152. The secondary component includes an exterior surface that consists of all surfaces except the interior surface. The component can contain one or more depressions 154 on the exterior surface of the component. Each depression 154 can be formed in the shape of a groove arranged in an orientation substantially along a perimeter arc of the component that can completely encircle the component, as shown. The depressions can, alternately, be randomly positioned discrete indentions. Each depression can be used to receive a length of suture may contribute to the overall flexibility of the component. The secondary component 150 can contain one or more prominences 156 on the interior surface of the component, which protrude from the interior surface. Each prominence can be arranged in an orientation substantially along a perimeter arc of the component that can completely encircle the component, as in an O-ring shape, as shown, or can be arranged in an orientation substantially parallel to the axis of rotation of the component. Alternately, the prominences 156 can be randomly positioned discrete nodules on the exterior surface of the component. The prominences 156 can be used to control the movement of said secondary component along the surface other structures as developed below by gripping a facing surface of the primary component.

The secondary component 150 can contain one or more depressions 160 on the interior surface of the component, which indent the interior surface. Each depression can be arranged in an orientation substantially along a perimeter arc of the component that can completely encircle the component, as in an O-ring shape, or can be arranged in an orientation substantially parallel to the axis of rotation of the component. The depressions 160 can be randomly positioned discrete indentions on the interior surface of the component. (See FIG. 9 which includes bumps 556 on an inner surface thereof.) The depressions 160 can be used to control the movement of said secondary component along the surface other structures as developed below by gripping a facing surface of the primary component. The secondary component can contain one or more fenestrations 158 along the body of said component that can create a passage from the exterior surface to the interior surface of the component, perpendicular to the axis of rotation of the component. The 158 fenestrations can be an opening in the body of the component or can be a weakened portion of the component that opens by force, like an old-fashioned rubber change pouch. The fenestrations 158 can be formed of a variety of shapes that can allow the component to change its configuration or overall shape along the axis of rotation as force is applied to the component. A fenestration can be any size and can, thus, can be sufficiently large as to leave only a small tether of material connecting portions of the component bordering the fenestration. In the example shown, the fenestration 158 is a weakened portion that opens by force. In the example of FIG. 10, below, the fenestration is an opening in the body of the component. The fenestrations 158 can allow the component to change its configuration along the axis of rotation as force is applied to the component.

Any embodiment of the primary component can be combined with any embodiment of the secondary component, according to the invention. In some applications, a device consisting of the first component, alone, may be utilized in a lattice application. In a device where a plurality of secondary components are combined with a single primary component, a single embodiment of the secondary component may be utilized in plurality; in an alternate arrangement, a variety of embodiments of the secondary component may be utilized. According to the invention, any primary component of the lattice stitch surgical tension-limiting device can feature or lack any combination of depressions, prominences and fenestrations in the body of the device as described above. Any secondary component of the lattice stitch surgical tension-limiting device can feature or lack any combination of depressions, prominences and fenestrations in the body of the device as described above. The device can be manufactured to size, or can be cut to size by the surgeon intra-operatively.

Figure 6:
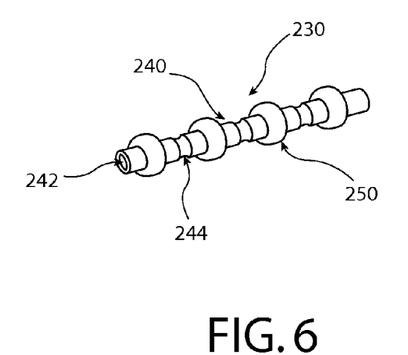
FIG. 6 is a top perspective view of another aspect of a lattice stitch surgical tension-limiting device according to the invention.

FIG. 6 shows a top perspective view of another aspect of the lattice stitch tension-limiting device. In this view, the device 230 consisting of a primary component 240 and a plurality of secondary components 250, according to the invention. In this embodiment, the primary component 240 has an elongated, semi-flexible and substantially cylindrical configuration with at least one patency 242 extending through the body of the component in an orientation substantially perpendicular to a plane extending through the rotational axis of the component, through which a length of suture may pass.

The primary component contains a plurality of depressions 244 on the external surface of the component. Each depression in this embodiment is arranged in a perimeter arc that completely encircles the component. The secondary component 250 of the device is substantially spherical in shape. In this embodiment of the lattice stitch tension-limiting device, the depressions 244 can be used to receive a length of suture.

Figure 7:
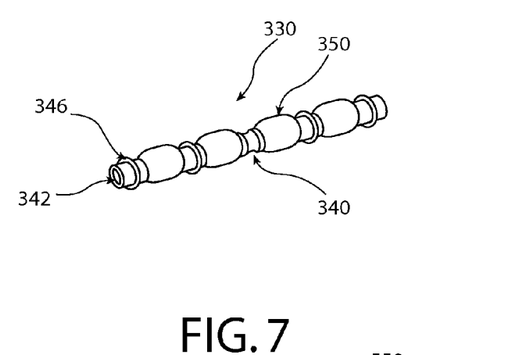
FIG. 7 is a top perspective view of another embodiment of a lattice stitch surgical tension-limiting device according to the invention.

FIG. 7 shows a top perspective view of another embodiment of the lattice stitch tension-limiting device. In this view the device 330 consisting of a primary component 340 and a plurality of secondary components 350, according to the invention. In this embodiment, the primary component 340 has an elongated, semi-flexible and substantially cylindrical configuration with at least one patency 342 extending through the body of the component in an orientation substantially perpendicular to a plane extending through the rotational axis of the component, through which a length of suture may pass. The primary component contains a plurality of prominences 346 on the external surface of the component. Each prominence is arranged in a perimeter arc that completely encircles the component. The secondary component 350 of the device is shaped substantially consistent with a prolate spheroid. In this embodiment of the lattice stitch tension-limiting device, the prominences 346 can be used to control the movement of the secondary components on the surface of the primary component, and can also be used to receive a length of suture.

Figures 8, 9:
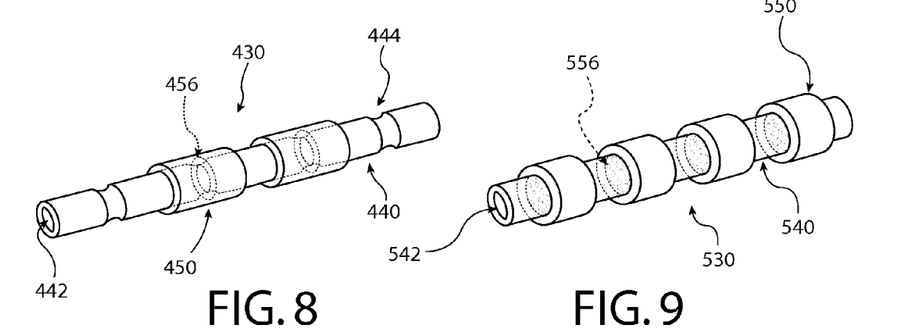
FIG. 8 is a top perspective view of another version of a lattice stitch surgical tension-limiting device according to the invention.
FIG. 9 is another aspect of a lattice stitch surgical tension-limiting device according to the invention.

Referring to FIG. 8 is a top perspective view of another version of the lattice stitch tension-limiting device. In this view the device 430 consisting of a primary component 440 and a plurality of secondary components 450, according to the invention. In this embodiment, the primary component 440 has an elongated, semi-flexible and substantially cylindrical configuration with at least one patency 442 extending through the body of the component in an orientation substantially perpendicular to a plane extending through the rotational axis of the component, through which a length of suture may pass. The primary component contains a plurality of depressions 444 on the external surface of the component. Each depression is arranged in a perimeter arc that completely encircles the component. The secondary component 450 of the device is shaped substantially consistent with a cylinder. Each secondary component in this embodiment contains a prominence 456 arranged in a perimeter arc that encircles the interior surface of the component. In this embodiment of the lattice stitch tension-limiting device, the prominences 456 in each secondary component can be used to control the movement of said secondary component on the surface of the primary component. Each depression 444 of the primary component can be used to control the movement of said secondary component on the external surface of the primary component, or can be used to receive a length of suture.

Referring to FIG. 9 is showing a top perspective view of another aspect of the lattice stitch tension-limiting device. In this view the device 530 consisting of a primary component 540 and a single of secondary component 550, according to the invention. In this embodiment, the primary component 540 has an elongated, semi-flexible and substantially cylindrical configuration with at least one patency 542 extending through the body of the component in an orientation substantially perpendicular to a plane extending through the rotational axis of the component, through which a length of suture may pass. The secondary component 550 of the device is shaped substantially consistent with a cylinder. Each secondary component 550 in this embodiment contains at least one prominence 556 on the interior surface of the component, and may be shaped as individual protrusions or protruding dimples. In this embodiment of the lattice stitch tension-limiting device 530, the prominences 556 in each secondary component can be used to control the movement of the secondary component on the surface of the primary component 540.

FIG. 10 is a top perspective view of another aspect of the lattice stitch tension-limiting device. In this view the device 630 consisting of a primary component 640 and a secondary component 650, according to the invention. In this embodiment, the primary component 640 has an elongated, semi-flexible and substantially cylindrical configuration with at least one patency 642 extending through the body of the component in an orientation substantially perpendicular to a plane extending through the rotational axis of the component, and a mouth 643, through which a length of suture may pass. The primary component contains a depression 644 on the external surface of the component. The depression 644 is arranged in a perimeter arc that completely encircles the component. The secondary component 650 of the device is shaped substantially consistent with a cylinder. The secondary component in this embodiment contains a prominence 656 arranged in a perimeter arc that encircles the interior surface of the component. The secondary component 650 also contains a plurality of fenestrations 658 in the body of the component that allow the component to change its configuration along the axis of rotation of the component 650 as force is applied to the component 650. In this embodiment of the lattice stitch tension-limiting device, the depression 644 of the primary component can be used to control the movement of said secondary component 650 on the external surface of the primary component. The prominence 656 of secondary component 650 can be used to control the movement of said secondary component on the surface of the primary component.

Alternative to the foregoing embodiments, in which the secondary component is movably disposed on the primary component, the secondary component may be attached in a fixed position on the exterior surface of the primary component. In other words, an interior surface of the secondary component is fixedly attached to the exterior surface of the primary component.

Figure 11:
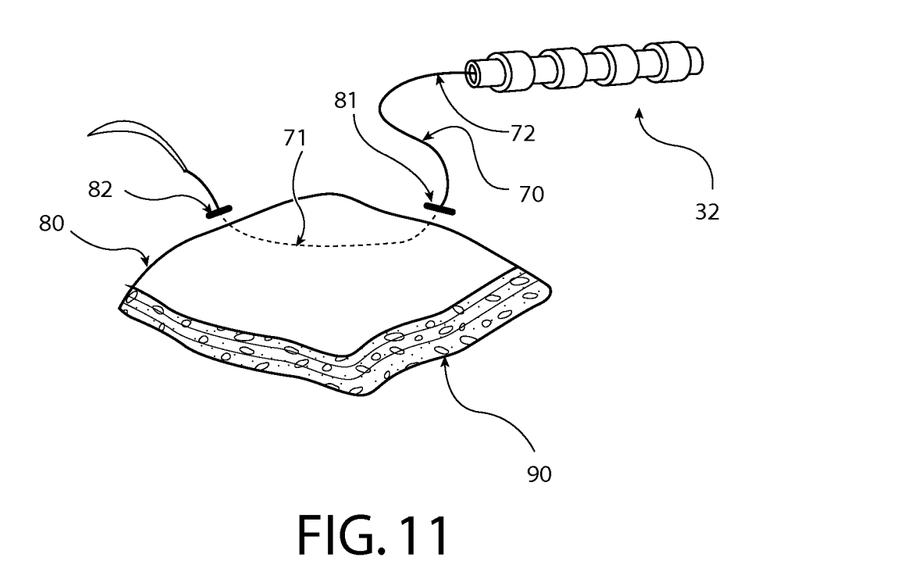
FIG. 11-13 are sequential partial sectional views, respectively, of a simple wound repair using the preferred embodiment of the lattice stitch and the lattice stitch surgical tension-limiting device 30 of FIG. 1 according to the invention.
Figure 12:
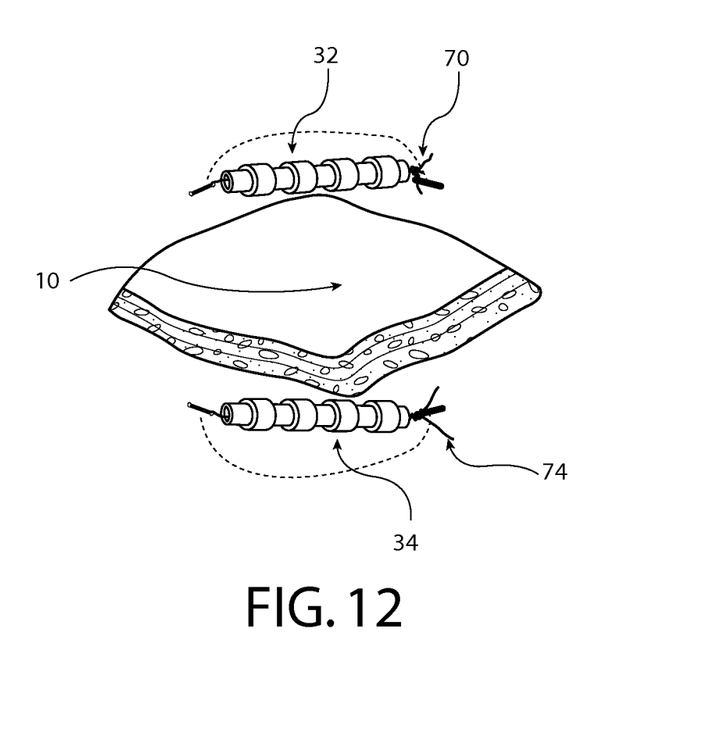
Figure 13:
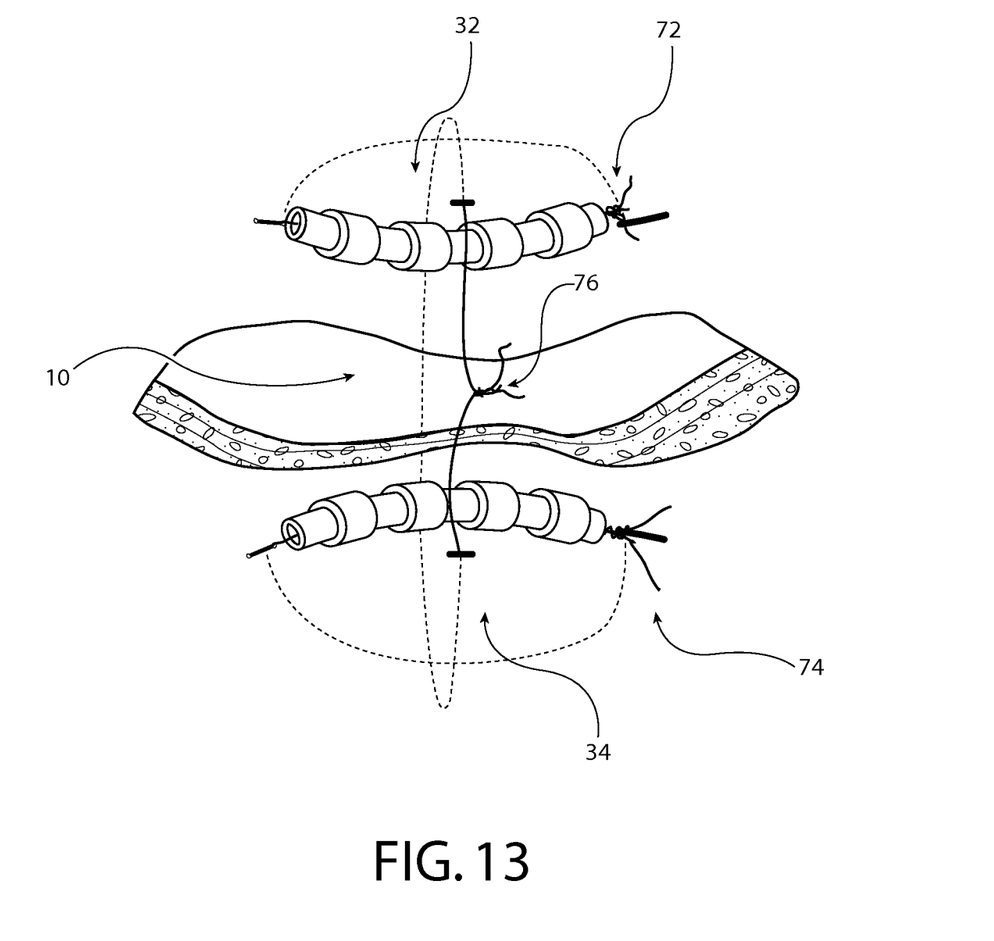

FIGS. 11-13 are sequential partial sectional views respectively of a lattice stitch repair using the lattice stitch surgical tension-limiting device of FIG. 1. Referring to FIG. 11, a length of suture 70 used to form the first anchor stitch portion of the lattice stitch is inserted into the tissues 80 in an orientation substantially parallel to the wound edge 90. The surgeon determines a proper length of a lattice stitch surgical tension-limiting device 32 needed by observing of the distance between entrance 81 and exit 82 points of a suture needle 71 in the tissue. A first tension-limiting device 32 of proper length then is inserted onto the free end of the suture 72 and is then tied to the surface of the tissues forming the first anchor stitch/device arrangement. In FIG. 12, a length of suture 74 used to form the second anchor stitch of the lattice stitch is used to attach a second tension-limiting device 34 to the surface of the tissues in a manner consistent with the method used attach the first device, in a location on the opposite side of a wound 10 to be repaired, in an opposed position to the first anchor stitch/device arrangement. In FIG. 13 a closing stitch 76 is arranged in the tissues around each anchor stitch/device arrangement and is drawn together and tied at the surface of the tissue, drawing the wound edges together to a closed condition. Any portion of any component of the lattice stitch tension-limiting device can be used by the closing stitch to draw the wound together to a closed condition. In an alternate embodiment, the closing stitch can be passed into

What is claimed is:

1. A lattice stitch surgical tension-limiting device configured to be placed on a surface of a body tissue between a length of suture and the surface of said body tissue comprising:
- a continuously flexible elongated member having a cylindrical cross sectional shape in at least one sectional axis of a body of said member;
- at least one patency extending though an entire length of the body of the member in an orientation substantially along the rotational axis of said member;
- an interior surface formed by an inner wall surface of said at least one patency, extending to each opening of said at least one patency;
- a patency mouth located at each opening of said patency;
- an exterior surface of the member defined by all surfaces of the member except the interior surface;
- wherein each patency mouth is a portion of the exterior surface of the member adjoining the interior surface of said member;
- said at least one patency configured to receive and retain a portion of suture used to make a lattice stitch so that the portion of suture extends along the entire length of the body of said member, and
- wherein said patency mouth is configured to interface with and allow movement of suture material on a surface of said patency mouth, and
- wherein a portion of the member is configured to move closer to an edge of a wound than remaining portions of said member, when said member is under an influence of a force exerted by a length of suture placed on the exterior surface of said member; and
- wherein force exerted by a length of suture on a portion of the patency mouth of said member causes a conformation change in said member near the patency mouth.

2. The lattice stitch surgical tension-limiting device as defined in claim 1, wherein the member includes at least one depression on the exterior surface, said at least one depression configured to receive a length of the suture used to make the lattice stitch.

3. The lattice stitch surgical tension-limiting device as defined in claim 1, wherein the member includes at least one prominence on the exterior surface, said at least one prominence configured to receive a length of the suture.

4. The lattice stitch surgical tension-limiting device as defined in claim 1, wherein the member is composed of layers of two or more chemically different materials.

5. The lattice stitch surgical tension-limiting device as defined in claim 1, wherein the device is impregnated with medications.

* * * * *